(12) United States Patent
Chappel (10) Patent No.: US 10,850,065 B2
(45) Date of Patent: Dec. 1, 2020

(54) CATHETER TIP ASSEMBLED WITH A SPRING

(75) Inventor: Shlomit Chappel, Ramat Hasharon (IL)

(73) Assignee: Medinol Ltd., Tel Aviv (IL)

( * ) Notice: Subject to any disclaimer, the term of this patent is extended or adjusted under 35 U.S.C. 154(b) by 428 days.

(21) Appl. No.: 13/022,749

(22) Filed: Feb. 8, 2011

(65) Prior Publication Data

US 2011/0196315 A1 Aug. 11, 2011

Related U.S. Application Data (60) Provisional application No. 61/303,276, filed on Feb. 10, 2010, provisional application No. 61/302,683, filed on Feb. 9, 2010.

(51) Int. Cl.
*A61M 25/00* (2006.01)
*A61M 25/10* (2013.01)

(52) U.S. Cl.
CPC . *A61M 25/0069* (2013.01); *A61M 2025/1093* (2013.01)

(58) Field of Classification Search
CPC ............ A61M 25/0012; A61M 25/005; A61M 25/0052; A61M 25/0053; A61M 25/0054; A61M 25/0069; A61M 25/008; A61M 25/0133; A61M 25/0141; A61M 25/0144; A61M 25/104; A61M 2025/091; A61M 2025/1093; A61M 25/10; A61M 2025/1043; A61M 2025/1063
USPC ......... 604/523–526, 528, 532; 606/191, 192, 606/194
See application file for complete search history.

(56) References Cited

U.S. PATENT DOCUMENTS

| | | |
|---|---|---|
| 1,899,914 A | 2/1933 | Pflueger |
| 3,618,613 A | 11/1971 | Schulte |
| 3,981,297 A | 9/1976 | Dunn et al. |

(Continued)

FOREIGN PATENT DOCUMENTS

| | | |
|---|---|---|
| CA | 2703926 | 5/2014 |
| CN | 101001658 | 7/2007 |

(Continued)

OTHER PUBLICATIONS

International Search Report and Written Opinion from corresponding PCT Application: PCT/IB2011/000386 dated Jun. 29, 2011, 12 pages.

(Continued)

*Primary Examiner* — Kami A Bosworth
(74) *Attorney, Agent, or Firm* — Cadwalader, Wickersham & Taft LLP (57) ABSTRACT

A catheter tip that provides longitudinal flexibility, pushability and radial rigidity thereby improving deliverability is provided. The catheter tip includes a spring-like element to provide longitudinal flexibility and pushability to the catheter tip. The spring-like element may also provide radial support to the distal edge of the catheter tip. Alternatively, a radially rigid distal end may also be included distal of the spring-like element. The apparatus may be used with any interventional catheter system, but is particularly suitable for use with balloon-expandable stent systems and balloon-angioplasty systems, where flexibility of the catheter tip and minimal flaring of the distal edge of the catheter tip is desirable.

47 Claims, 4 Drawing Sheets

(56) References Cited

U.S. PATENT DOCUMENTS

| | | | |
|---|---|---|---|
| 4,044,765 A | 8/1977 | Kline | |
| 4,215,703 A | 8/1980 | Willson | |
| 4,616,652 A * | 10/1986 | Simpson | A61M 25/104 600/434 |
| 4,665,604 A | 5/1987 | Dubowik | |
| 4,705,511 A | 11/1987 | Kocak | |
| 4,734,093 A | 3/1988 | Bonello et al. | |
| 4,838,268 A * | 6/1989 | Keith | A61M 25/104 604/103.1 |
| 4,846,174 A * | 7/1989 | Willard | A61M 25/09041 604/913 |
| 4,927,413 A * | 5/1990 | Hess | A61B 17/22 604/913 |
| 4,985,022 A * | 1/1991 | Fearnot | A61M 25/0045 604/288 |
| 5,112,304 A | 5/1992 | Barlow et al. | |
| 5,195,954 A | 3/1993 | Schnepp-Pesch | |
| 5,234,451 A | 8/1993 | Osypka | |
| 5,243,997 A | 9/1993 | Uflacker et al. | |
| 5,256,145 A | 10/1993 | Atkinson et al. | |
| 5,279,596 A | 1/1994 | Castaneda et al. | |
| 5,308,324 A | 5/1994 | Hammerslag et al. | |
| 5,344,395 A | 9/1994 | Whalen et al. | |
| 5,378,234 A * | 1/1995 | Hammerslag | A61M 25/0053 138/129 |
| 5,387,225 A * | 2/1995 | Euteneuer | A61M 25/0029 604/913 |
| 5,397,305 A | 3/1995 | Kawula et al. | |
| 5,409,470 A * | 4/1995 | McIntyre | A61M 25/09 604/528 |
| 5,423,755 A | 6/1995 | Kesten et al. | |
| 5,458,585 A | 10/1995 | Salmon et al. | |
| 5,569,197 A * | 10/1996 | Helmus | A61M 25/09 604/102.02 |
| 5,571,073 A | 11/1996 | Castillo | |
| 5,573,520 A * | 11/1996 | Schwartz | A61M 25/0013 604/264 |
| 5,607,407 A * | 3/1997 | Tolkoff | A61M 25/005 604/523 |
| 5,626,593 A | 5/1997 | Imran | |
| 5,695,506 A * | 12/1997 | Pike | A61B 17/320783 604/22 |
| 5,833,631 A | 11/1998 | Nguyen | |
| 5,865,767 A | 2/1999 | Frechette et al. | |
| 5,972,019 A | 10/1999 | Engelson et al. | |
| 5,989,208 A | 11/1999 | Nita | |
| 6,069,965 A | 5/2000 | Takewa et al. | |
| 6,398,791 B1 * | 6/2002 | Que | A61B 17/221 604/264 |
| 6,440,120 B1 * | 8/2002 | Maahs | 604/523 |
| 6,500,147 B2 * | 12/2002 | Omaleki et al. | 604/103.09 |
| 6,589,253 B1 | 7/2003 | Cornish et al. | |
| 8,034,045 B1 | 10/2011 | Lyons | |
| 2001/0007938 A1 | 7/2001 | Long | |
| 2002/0010420 A1 | 1/2002 | Bagaoisan et al. | |
| 2002/0065475 A1 | 5/2002 | Meguro et al. | |
| 2002/0072730 A1 * | 6/2002 | McGill et al. | 604/525 |
| 2003/0018318 A1 * | 1/2003 | Melsky | 604/526 |
| 2003/0028153 A1 * | 2/2003 | Brennan | A61M 25/0662 604/263 |
| 2003/0191434 A1 | 10/2003 | Dorros et al. | |
| 2004/0030375 A1 | 2/2004 | Pierce | |
| 2005/0119606 A1 | 6/2005 | Nita | |
| 2005/0154443 A1 | 7/2005 | Linder et al. | |
| 2005/0245894 A1 | 11/2005 | Zadno-Azizi | |
| 2006/0100602 A1 * | 5/2006 | Klint | A61B 17/12022 604/524 |
| 2006/0178653 A1 | 8/2006 | Shimogami et al. | |
| 2007/0135830 A1 * | 6/2007 | Schaeffer | A61M 25/0068 606/192 |
| 2007/0240817 A1 | 10/2007 | Strong et al. | |
| 2007/0260224 A1 | 11/2007 | Von Oepen et al. | |
| 2008/0108974 A1 * | 5/2008 | Yee Roth | A61L 29/085 604/529 |
| 2009/0082723 A1 | 3/2009 | Krogh et al. | |
| 2009/0125043 A1 | 5/2009 | Dehnad | |
| 2009/0149777 A1 | 6/2009 | Rooney et al. | |
| 2009/0264910 A1 | 10/2009 | Laufer | |
| 2009/0292296 A1 | 11/2009 | Pansky et al. | |
| 2010/0049167 A1 | 2/2010 | Myers | |
| 2011/0196384 A1 | 8/2011 | Pansky | |
| 2011/0245775 A1 | 10/2011 | Tekulve | |
| 2011/0288532 A1 | 11/2011 | Faherty et al. | |
| 2012/0130300 A1 | 5/2012 | Stavchansky et al. | |
| 2012/0165789 A1 | 6/2012 | Deckard et al. | |
| 2012/0165850 A1 | 6/2012 | Deckard et al. | |
| 2012/0323145 A1 | 12/2012 | Nagano et al. | |

FOREIGN PATENT DOCUMENTS

| | | |
|---|---|---|
| CN | 101926667 A | 12/2010 |
| CN | 102205165 | 10/2011 |
| DE | 4036570 A1 | 5/1992 |
| EA | 005391 | 2/2005 |
| EP | 0443256 A1 | 8/1991 |
| EP | 1 339 355 | 9/2003 |
| JP | 63-238873 | 10/1988 |
| JP | H01-117357 | 8/1989 |
| JP | H05-261114 | 10/1993 |
| JP | H06-23053 | 2/1994 |
| JP | H07-236695 | 9/1995 |
| JP | H08-501945 | 3/1996 |
| JP | 2682831 B | 8/1997 |
| JP | 2000-502264 A | 2/2000 |
| JP | 2001-129002 A | 5/2001 |
| JP | 2001-157712 | 6/2001 |
| JP | 2001-204825 | 7/2001 |
| JP | 2002-224221 | 8/2002 |
| JP | 2003-520651 | 7/2003 |
| JP | 2003-521279 | 7/2003 |
| JP | 2005-511108 | 4/2005 |
| JP | 3638304 | 4/2005 |
| JP | 2006-271901 | 10/2006 |
| JP | 2010-022566 A | 2/2010 |
| JP | 2010-513034 A | 4/2010 |
| JP | 2011-078525 | 4/2011 |
| JP | 2011512956 A | 4/2011 |
| JP | 2013-518691 | 5/2013 |
| JP | 2013-518693 | 5/2013 |
| RU | 98112572 | 5/2000 |
| RU | 2207823 | 7/2003 |
| RU | 2302267 C2 | 7/2007 |
| RU | 91674 U1 | 2/2010 |
| SU | 1528505 A1 | 12/1989 |
| WO | WO 93/11711 | 6/1993 |
| WO | WO 96/08196 A1 | 3/1996 |
| WO | WO 97/19644 | 6/1997 |
| WO | WO 01/08737 | 2/2001 |
| WO | WO 01/51114 | 7/2001 |
| WO | WO 2006/042157 | 4/2006 |
| WO | WO 2006/093274 | 9/2006 |
| WO | WO 2008/019696 | 2/2008 |
| WO | WO 2009/108816 | 9/2009 |
| WO | WO 2009/141810 A2 | 11/2009 |
| WO | WO 2013/012528 | 1/2013 |

OTHER PUBLICATIONS

International Search Report and Written Opinion from related PCT Application No. PCT/IB2014/000699 dated Nov. 7, 2014, 13 pages.
Extended European Search Report from related EP Application No. 18150461.4 dated Apr. 6, 2018, 9 pages.
Russian Search Report from related application No. RU 2016129732 dated Jun. 8, 2018, 4 pages.
Extended European Search Report from related application No. EP 18151191.6 dated Apr. 24, 2018, 8 pages.
International Search Report and Written Opinion from related PCT Application No. PCT/IB2014/003282 dated Feb. 5, 2016, 14 pages.
International Search Report and Written Opinion from related PCT Application No. PCT/IB2011/000401 dated Jul. 6, 2011, 16 pages.

(56) References Cited

OTHER PUBLICATIONS

Russian Search Report from related application No. RU 2014148109 dated Jun. 2, 2016, 4 pages.
Russian Search Report from related application No. RU 2016129731 dated Jan. 18, 2018, 4 pages.
Spring. (n.d.) Random House Kerneman Webster's College Dictionary. (2010). Retrieved Jun. 25, 2016 from http://www.thefreedictionary.com/spring.

* cited by examiner

CATHETER TIP ASSEMBLED WITH A SPRING

This application claims the benefit of priority to U.S. Provisional Application No. 61/303,276, filed Feb. 10, 2010, and to U.S. Provisional Application No. 61/302,683, filed Feb. 9, 2010, all of which are incorporated herein by reference in their entirety.

FIELD OF THE INVENTION

The present invention relates to an endovascular catheter, in particular a flexible catheter tip for use, for example, for stent delivery and percutaneous angioplasty. The catheter tip of the invention is specially designed to have features especially useful in percutaneous procedures in which the catheter must traverse stenotic blood vessels, tortuous vessels, or vessels containing previously deployed stents.

BACKGROUND

In standard stent delivery systems, the proximal portion of the catheter is manufactured from materials that make it relatively stiff or inflexible, which endows the catheter with adequate pushability. By contrast, the distal portion of the catheter is manufactured to be rather flexible to allow adequate deliverability of the stent through tortuous vessels to the desired target.

In the case of a balloon catheter, the balloon, which is located at the distal portion of the catheter, is delivered in a deflated state, wrapped around the catheter's inner inflation tube and covered by a crimped stent. Distal to the balloon, the catheter tip is usually tapered, wherein the balloon distal shoulder is fused to the catheter's inner inflation tube. The whole catheter is designed to glide on a guide wire, with the catheter tip serving as the leading part of the catheter to, for example, penetrate a lesion, navigate through a curved vessel, or pass through an already deployed stent within the vessel.

The properties of the catheter tip determine to a large extent whether or not the catheter will catch on the rough surface of the vessel, the surface of vessel lesion or obstruction, or the struts of a previously deployed stent.

Current catheter tips of stent delivery systems and on angioplasty balloon systems are made of plastic material, are generally tapered, and have a tip shape that is aimed to provide deliverability of the catheter through challenging anatomies. Two parameters may be adjusted to optimize deliverability. The catheter tip may be designed to have longitudinal flexibility to accommodate tortuous vessels, and/or the tip shape and its radial rigidity may be modified to avoid collapse of the distal edge of the tip and/or kinking of the proximal neck of the catheter tip when obstacles are encountered. Optimizing both parameters simultaneously in a catheter tip is problematic, as longitudinal flexibility requires a very thin or flexible material, while pushability and radial rigidity require a thick or stiff material.

Therefore, there is a need in the art for an endovascular catheter tip that is longitudinally flexible and pushable and has radial rigidity at its distal end—in particular at the distal edge, to optimize deliverability of the catheter.

SUMMARY OF THE INVENTION

The present invention provides an endovascular catheter tip having longitudinal flexibility, pushability and radial rigidity at its distal end. By longitudinal flexibility is meant an ability to bend along the longitudinal axis (e.g., to facilitate navigation through tortuous vessels). The catheter tip of the invention includes two components. The first component of the catheter tip includes a spring-like structure that endows the catheter tip with the desired longitudinal flexibility and pushability. The second component of the catheter tip—the distal end—provides radial rigidity and is rounded and tapered to prevent the distal edge from flaring and catching on, for example, plaque or the strut of a previously implanted stent as the catheter is moved through the vessel. Thus, for example, the distal end can be made of a sufficiently thick or stiff material to confer radial rigidity. By so combining these two components in one catheter tip, the present invention provides a device having otherwise conflicting structural and functional parameters for optimizing deliverability of the catheter.

In another embodiment, a single component, a spring-like structure, provides longitudinal flexibility and pushability to the catheter tip and radial rigidity at the distal end of the catheter tip.

In yet another embodiment, the catheter tip further includes a flexible tube, contiguous with the distal end of the balloon and attached to or integrated with the spring-like element that, in conjunction with the spring-like element, confers longitudinal flexibility to the catheter tip.

The apparatus of the invention may be used, for example, for intravascular delivery of prosthetic devices, such as a stent, or for balloon angioplasty. Where a balloon catheter is used, the catheter tip constitutes the portion of the catheter distal to the balloon. In embodiments where the catheter does not have a balloon mounted on it, for example in biliary stent systems where the catheter itself may be expandable, the catheter tip of the invention may be mounted at the end of the expandable catheter to lead the catheter through the biliary duct. Generally, the catheter tip may extend a few millimeters beyond the distal edge of such a catheter.

In addition to the advantage of enhanced deliverability parameters, another desirable effect of the catheter tip of the invention is higher radio-opacity, which may provide the operator with valuable feedback regarding position of the catheter tip during insertion of the catheter into the anatomy to be treated.

DETAILED DESCRIPTION

In order to enhance deliverability of an endovascular catheter by combining two otherwise contradictory parameters into one catheter tip, the apparatus of the invention provides a catheter tip having longitudinal flexibility, pushability and radial rigidity. In particular, the catheter tip of the invention includes a spring-like element that is not only longitudinally flexible, but also can provide pushability to the catheter tip and may also have radial rigidity, meaning that it can provide radial support to the catheter tip. The catheter tip of the invention may also include a distal end that extends beyond the distal end of the spring-like element. The distal end preferably is made of a material that confers pushability to the tip and has a tapered shape and sufficient radial rigidity to prevent or minimize flaring at the distal edge of the catheter tip, while gliding over a curved guide wire.

The novel combined features of the present invention permit an operator to guide an endovascular catheter over a guide wire through tortuous vessels, lesioned or stenotic vessels, or stented vessels with minimal risk of having the distal edge of the catheter tip catch on rough surfaces of the lumen wall or a previously implanted stent and also minimize the risk that the flexible catheter tip will buckle or collapse against the resistance of a vessel stenosis or occlusion.

The apparatus of the invention is discussed and explained below with reference to the accompanying drawings. Note that the drawings are provided as an exemplary understanding of the present invention and to schematically illustrate particular embodiments of the present invention. The skilled artisan will readily recognize other similar examples equally within the scope of the invention. The drawings are not intended to limit the scope of the present invention as defined in the appended claims.

Figure 1:
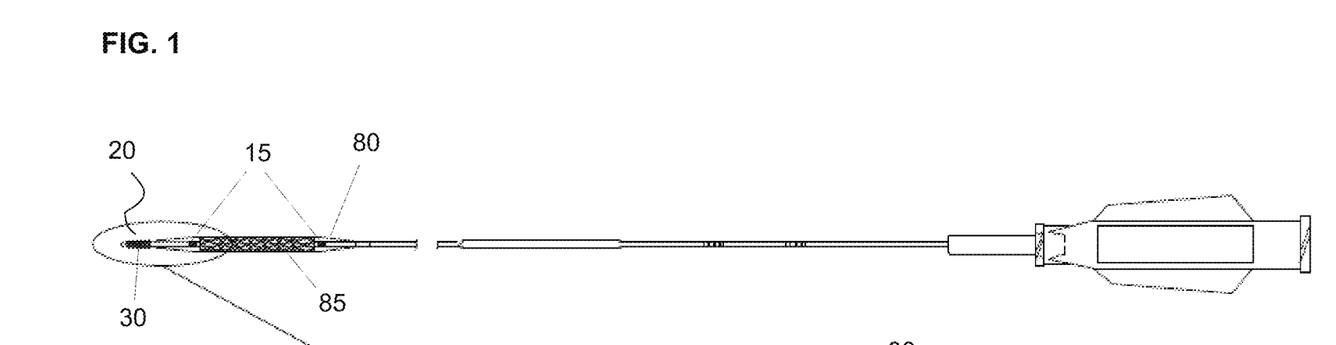
FIG. 1 depicts an embodiment of the catheter tip of the invention that includes a spring-like element, on a stent delivery system.
Figure 1A:
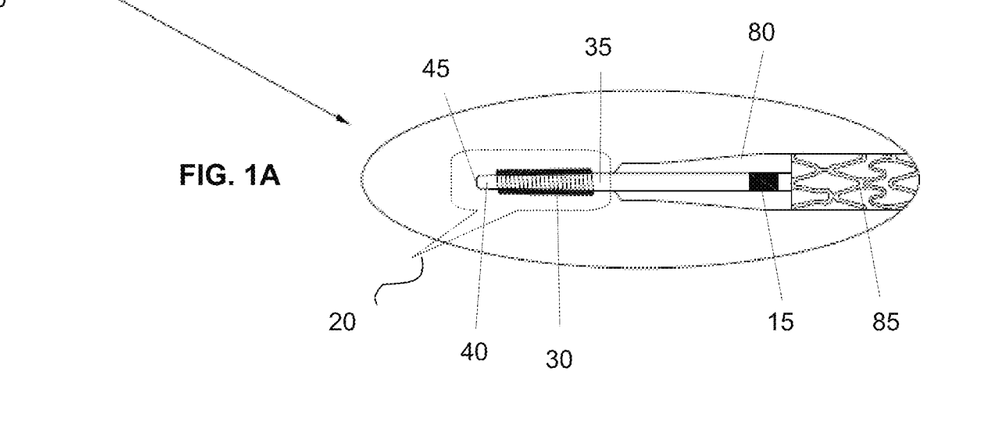
FIG. 1A shows the position of the spring-like element on the catheter tip.

The catheter tip of the invention includes a spring-like element, which provides not only longitudinal flexibility, but also pushability to the catheter tip. The spring-like element may also confer radial rigidity to the catheter tip. An embodiment of the catheter tip 20 of the invention is illustrated in FIGS. 1 and 1A on a balloon-expandable stent delivery system. Depicted in FIG. 1 are a balloon 80, a balloon-expandable stent 85, optional radiopaque markers 15, and the catheter tip 20 including a spring-like element 30. While illustrated here on a balloon-expandable stent system, the catheter tip 20 may be used on any catheter that must navigate tortuous or partially obstructed lumens. As shown in more detail in FIG. 1A, this embodiment of catheter tip 20 of the invention includes a spring-like element 30, such as, in this embodiment, an extension spring. The spring-like element 30 may have a single diameter from its proximal to distal end, or it may taper towards the distal end.

As shown in FIGS. 1 and 1A, where the catheter tip is used on a balloon-expandable stent system, the spring-like element 30 is positioned distal to the balloon 80. The spring-like element 30 may abut the balloon shoulder. Alternatively, as shown in FIG. 1, the spring-like element 30 may be positioned a distance away from the balloon shoulder, in the distal direction, for example 1 or 2 mm, or in the proximal direction, up to the middle of the balloon or the proximal bond (i.e., juncture between the balloon and the outer tube). Alternatively, the spring-like element is positioned approximately 0.5 mm proximal of the distal edge 45 of the catheter tip 20. The portion of the catheter tip 20 that extends distal of the spring-like element 30 to the distal edge 45 is the distal end portion 40 of the catheter tip 20. The distal end portion 40 may have sufficient stiffness to provide both pushability and radial rigidity. In one embodiment, the distal end portion 40 may be made of a stiff material such as polyamide. In another embodiment (not shown), the spring-like element 30 may extend to the distal edge 45 of the catheter tip 20 and provide radial rigidity to the distal end portion 40 of the catheter tip 20. In this other embodiment, the spring-like element 30 may be tapered toward its distal end, but it need not be.

Where the spring-like element 30 is positioned at a distance from the shoulder of the balloon 80, as illustrated in FIG. 1, the catheter tip 20 may include a spacer portion 35 that bridges the distance between the distal end of the balloon 80 and the proximal end of the spring-like element 30. The spacer portion 35 may be a longitudinally flexible tube. In one embodiment, the spacer portion 35 connects the distal end of the balloon shoulder to the proximal end of the spring-like element 30. Materials used to manufacture the spacer portion 35 may include, for example, polyether block amide (PEBAX). Alternatively, the spacer portion 35 may be an extension of a flexible tube into which the spring-like element 30 is inserted. Examples of suitable materials for the flexible tube include a block co-polymer, such as PEBAX, polyurethane, or similar appropriate materials. Such a flexible tube may extend just beyond the distal end of the spring-like element 30, where it is contiguous with the proximal end of the distal end portion 40. The distal end portion 40 of the catheter tip 20 may be formed from a plastic tube manufactured materials such as Nylon, PEBAX, or various co-polymers. Tapering of the distal end portion 40 may be effected by heating. The various tubes and spring member may be connected by thermal fusing.

Figures 2A, 2B:
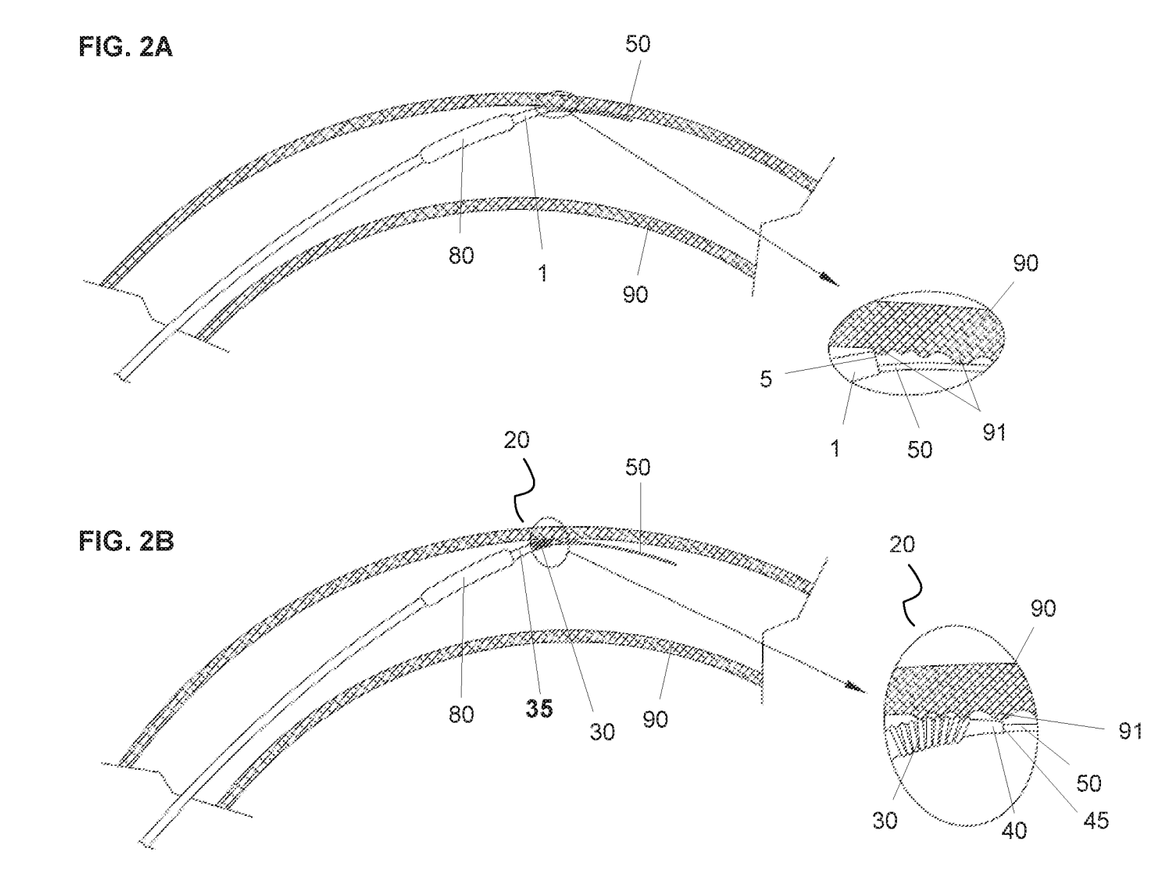
FIG. 2A depicts the conventional catheter tip on a balloon catheter system in a curved vessel.
FIG. 2B depicts an embodiment of the flexible catheter tip of the invention on a balloon catheter in a curved vessel.

FIG. 2A depicts how a conventional catheter tip made of a stiff material to achieve good pushability may catch on the rough surface of the lumen of a curved vessel. Depicted in FIG. 2A is a conventional catheter tip 1; a balloon 80 of a balloon-catheter on which the conventional catheter tip 1 is mounted for illustration; and a guide wire 50. As the guide wire 50 contacts a curved portion of a vessel wall 90, it tends to bend longitudinally as shown in FIG. 2A. The conventional catheter tip 1 has less longitudinal flexibility than the guide wire 50. Thus, as shown in more detail in the inset of FIG. 2A, the distal edge 5 of the conventional stiff catheter tip 1 protrudes away from the bent guide wire 50 toward the vessel wall where it can catch on the rough surface 91 of the lumen of the vessel wall 90, making deliverability of the catheter difficult and potentially causing damage to the vessel wall 90. Similarly, where the catheter must traverse a stented vessel, the protruding distal edge 5 of such a conventional device can catch on struts or other structures of the previously deployed stent.

FIG. 2B, illustrates features of an embodiment of the present invention that minimize the risk that the distal edge of the catheter tip will catch on the rough surface of the lumen wall of a curved vessel. Specifically, FIG. 2B shows a catheter tip 20 made up of two sections—a flexible section with a pushability characteristic, including a spring-like element 30, and a stiff and radially rigid section at the distal end 40, in a curved vessel, and a balloon 80 of a balloon-catheter on which the catheter tip 20 is mounted for illustration. The inset of FIG. 2B shows in greater detail the longitudinal flexibility of the spring-like element 30. The longitudinal flexibility of the spring-like element 30 permits the catheter tip 20 to flex easily with the guide wire 50 as it flexes laterally with the curve of the vessel lumen, so that the distal end 40 can track tightly with the guide wire 50 and the distal edge 45 does not protrude and catch on the rough surface 91 of the lumen of the vessel wall 90. In this embodiment, the distal end 40 is tapered, as illustrated in the inset of FIG. 2B, which tapering may further reduce the risk that the distal edge 45 will catch on the rough surface 91 of the lumen of the vessel wall 90. In this or any of the other embodiments where the spring-like element 20 is not inserted into a flexible tube, the spring-like element 20 may be covered with or embedded in a layer of a flexible polymer or similar material to create a smooth surface and improve trackability of the structure without altering the flexible properties of the spring. Examples of materials for such coverings include polyurethane and PEBAX.

Figures 3A, 3B:
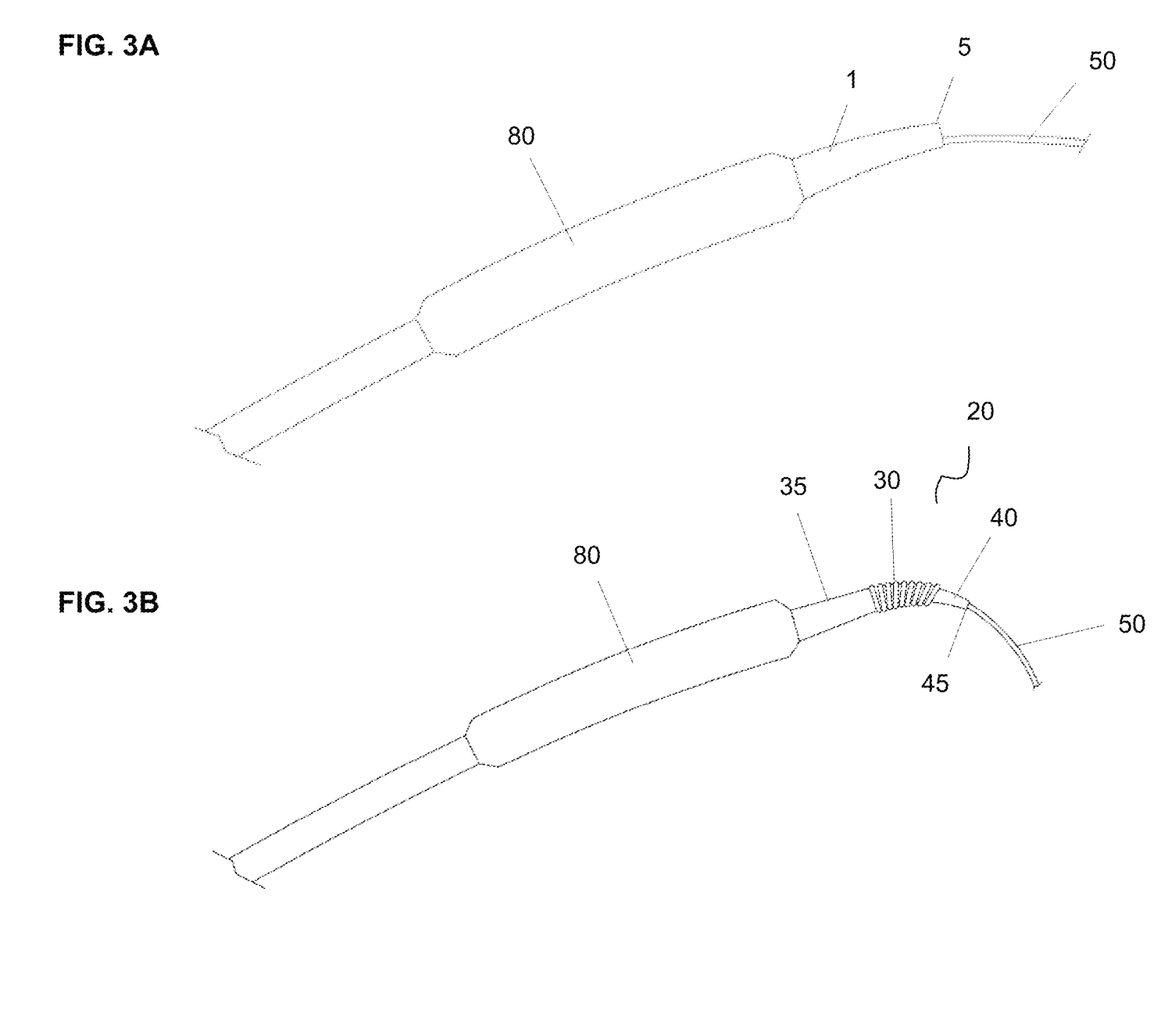
FIG. 3A depicts tip edge protrusion of a conventional catheter tip.
FIG. 3B depicts absence of tip edge protrusion of an embodiment of the flexible catheter tip of the invention having a spring-like element and a radially rigid distal end.

FIG. 3A illustrates a conventional catheter tip 1 mounted on a balloon-angioplasty system, also showing the balloon 80, and the problem in the art of protrusion of the distal edge 5 of the catheter tip 1. The lack of flexibility and the radial rigidity along the length of the conventional catheter tip 1 tends to cause the distal edge 5a of the conventional catheter tip 1 to protrude away from the guide wire 50 as it curves through the vessel. The large inner diameter and thick walls of the distal end of the conventional catheter tip may further contribute to the problem of the protruding distal edge.

By contrast, FIG. 3B illustrates how the combination of flexibility and radial rigidity of a catheter tip 20 in accordance with the invention minimizes flaring of the distal edge 45 in an embodiment of the catheter tip of the invention (also mounted on a catheter of a balloon-angioplasty system). Depicted in FIG. 3B is a catheter tip 20 including a spacer portion 35, a spring-like element 30, and a distal end 40; the balloon 80 of the balloon-angioplasty system; and a guide wire 50. The radial rigidity and the tapered shape of the distal end 40 in combination with the flexibility of the spring-like element 30 limits protrusion of the distal edge 45 beyond the guide wire. The longitudinal flexibility of the spring-like element 30 permits the catheter tip 20 to bend with the guide wire, minimizing force on the distal edge 45 from the guide wire, and the radial rigidity of the distal end 40 minimizes plastic deformation. As shown in FIG. 3B, bending of the guide wire 50 does not result in protrusion of the distal edge 45 of such a catheter tip 20 from the guide wire 50. In the embodiment illustrated in FIG. 3B, the distal end 40 may be made of material having sufficient radial rigidity and stiffness to provide pushability. In another embodiment, radial rigidity of the distal edge 45 may be provided by the spring-like element 30 itself (not shown). In such embodiments, it is preferable for the spring-like element 30 to extend to the distal edge 45 of the catheter tip 20, or close to the distal edge 45, so as to provide pushability and radial rigidity to the distal end of the catheter tip 20. Preferably, in this other embodiment the spring-like element 30 is tapered.

Figure 4A:
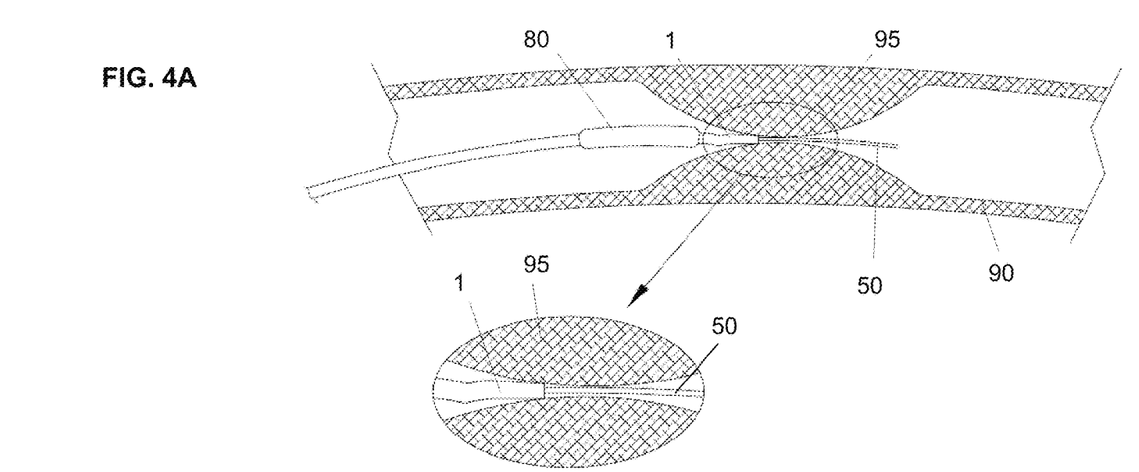
FIG. 4A depicts a conventional catheter tip on a balloon catheter in a stenotic vessel.

The estimated compromise between rigidity and elasticity maintained by a conventional catheter tip may result in kinking when the catheter tip encounters a stenotic portion of a vessel, as illustrated in FIG. 4A. For example, kinking may occur near the distal end of the balloon or any other localized soft or elastic point within the catheter tip. A conventional catheter tip on a balloon catheter is shown in FIG. 4A being pushed through a blood vessel 90 having a stenosis 95. Also depicted is the balloon 80 for the balloon-angioplasty balloon, on which the conventional catheter tip 1 is mounted for illustration, and a guide wire 50. As the conventional catheter tip is advanced through the stenosis 95, the stenotic material causes friction or resistance against the catheter tip, causing the conventional catheter tip 1 to give way to the harder material of the vessel plaque, causing it to kink or buckle, as shown in the insert of FIG. 4A. This is particularly a problem when stenotic material includes significant calcium deposits, which is not uncommon.

Figure 4B:
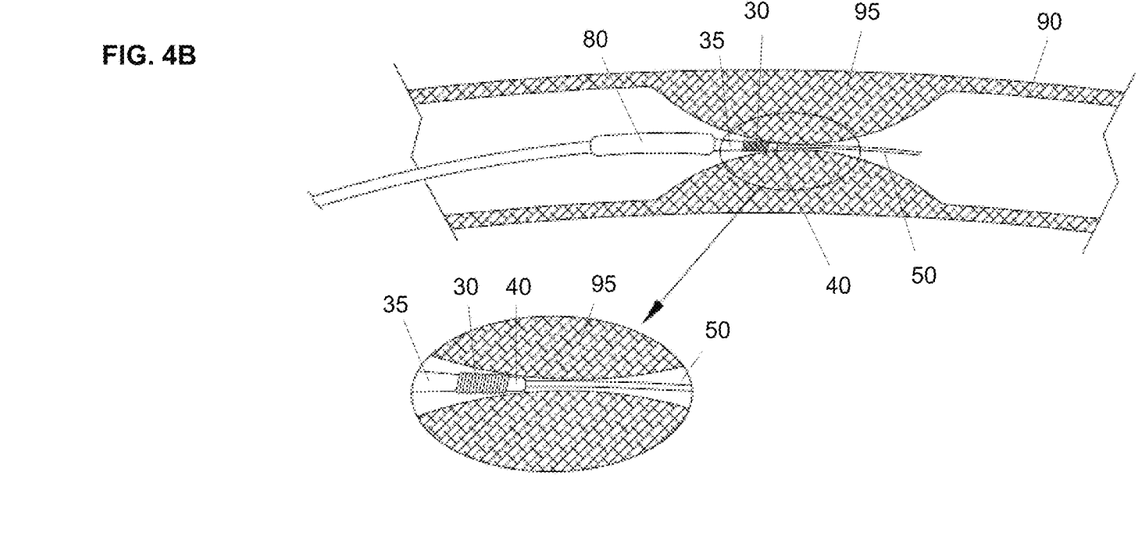
FIG. 4B depicts an embodiment of the flexible, pushable catheter tip of the invention on a balloon catheter system in a stenotic vessel.

By contrast, the flexible catheter tip of the invention provides greater pushability, and it exhibits no kinking because of its flexible body and spacer portion. This is illustrated in FIG. 4B, where an embodiment of the invention mounted on a balloon catheter is shown being pushed through a stenotic vessel. Depicted is a catheter tip including a spring-like element 30, a spacer portion 35, and a distal end; the balloon 80 of a balloon-angioplasty system on which the catheter tip is mounted for illustration; and a guide wire 50. Because the spring-like element 30 may provide not only longitudinal flexibility and radial support, but also improved pushability to the catheter tip 20, the friction exerted by the stenosis 95 against the catheter tip of the invention will not cause the catheter tip 20 to kink. With regard to the distal end 40 of the catheter tip 20 of the invention, in this embodiment, the spring-like element 30 itself may provide sufficient pushability to the distal end 40, and/or the distal end 40 may be made of a sufficiently stiff or thick material to provide pushability, as well as sufficient radial rigidity.

Any structure that has the desired properties of longitudinal flexibility, radial rigidity and pushability is suitable as a spring-like element in accordance with the invention. Examples of a spring-like element include an extension spring, an accordion plastic tube, and a braided-accordion plastic tube. Some springs, including for example compression springs, are not preferred as spring-like elements. Extension springs have a tightly packed coil that is conducive to flexion along the longitudinal axis, without permitting spring compression or deformation, which could negatively impact the pushability of the catheter or control of the catheter tip when the catheter is pushed.

Suitable materials for the spring-like element include, for example, stainless steel, cobalt chromium, Nitinol or other appropriate materials that would be apparent to one skilled in the art from the description herein. A suitable range for a spring constant for the spring-like element is 0.3-25 gF/mm. Where the spring-like element is made of a coiled wire—for example, a stainless steel wire—the diameter of the wire may be in the range of 0.04-0.3 mm, preferably, 0.06-0.2 mm. One skilled in the art would appreciate from these parameters the appropriate wire diameter range for a spring-like element constructed from other materials. The spring-like element may be constructed using radiopaque materials to provide the catheter tip with higher radiopacity, thereby allowing improved imaging of the catheter tip.

The embodiments of the catheter tips of the invention are illustrated and described herein mounted on catheters of balloon-expandable stent systems and balloon angioplasty systems. However, it is contemplated the catheter tips may be used on any intravascular catheters, including for example self-expanding stent systems, intravascular catheters used to deliver other intravascular prosthetic devices, or other therapeutic intravascular catheters.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:
1. A flexible and pushable catheter tip, comprising:
a longitudinally flexible tube having a luminal side and a vessel wall side; and a spring-like element, said spring-like element attached to said flexible tube, said spring-like element located at a position selected from the group consisting of: inside said flexible tube, and outside said flexible tube;
wherein said spring-like element provides pushability to said catheter tip,
wherein said spring-like element extends to a distal edge of said catheter tip, and
wherein a spring constant for the spring-like element is in a range of 0.3 to 25 gF/mm.

2. The catheter tip of claim 1, further comprising a spacer portion located at a proximal end of said spring-like element.

3. A flexible and pushable catheter tip, comprising:
a longitudinally flexible tube having a luminal side and a vessel wall side;
a spring-like element having a distal end, said spring-like element coupled with said longitudinally flexible tube, said spring-like element located on the luminal side of said flexible tube; and
a radially rigid distal end section located distal of said spring-like element and contiguous with a structure selected from the group consisting of: said longitudinally flexible tube and said spring-like element,
wherein said spring-like element provides pushability to said catheter tip, and
wherein a spring constant for the spring-like element is in a range of 0.3 to 25 gF/mm.

4. The catheter tip of claim 3, wherein said radially rigid distal end section tapers distally.

5. The catheter tip of claim 3, further comprising a spacer portion located at a proximal end of said spring-like element.

6. The catheter tip of claim 3, wherein a material of the longitudinally flexible tube is a flexible polymer material selected from the group consisting of: block co-polymer, polyether block amide (PEBA), and polyurethane, and wherein a material of the radially rigid distal end section is selected from the group consisting of:
polyamide, nylon, PEBA, and a co-polymer material.

7. A flexible and pushable catheter tip, comprising:
a non-compressible spring-like element; and
a spacer portion located at a proximal end of said spring-like element;
wherein said spring-like element provides pushability to said catheter tip;
wherein said spring-like element is a wire coil, and
wherein a spring constant for the spring-like element is in a range of 0.3 to 25 gF/mm.

8. The catheter tip of claim 7, wherein said catheter tip further comprises a radially rigid distal end section located distal of said spring-like element and contiguous thereto.

9. The catheter tip of claim 8, wherein said spacer portion is a longitudinally flexible tube that extends to at least a distal edge of said spring-like element.

10. The catheter tip of claim 8, wherein said spacer portion is a longitudinally flexible tube that extends to a proximal edge of said spring-like element.

11. The catheter tip of any one of claims 8-10, wherein at least one of said spring-like element or said radially rigid distal end section is tapered distally.

12. The catheter tip of claim 7, wherein said spring-like element extends to a distal edge of said catheter tip.

13. The catheter tip of claim 12, wherein said spring-like element tapers toward said distal edge of said catheter tip.

14. The catheter tip of claim 7, wherein said spacer portion is a longitudinally flexible tube and spring-like element is inserted at least in part into said spacer portion.

15. A catheter, comprising: a proximal end; a distal end; a balloon having a proximal shoulder and a distal shoulder; and a catheter tip, said catheter tip including a spring-like element having a length, and a longitudinally flexible tube extending with the entire length of said spring-like element;
wherein said spring-like element provides pushability to said catheter tip and said balloon is mounted on said catheter proximal of said catheter tip,
wherein said spring-like element has a distal end and does not extend to a distal edge of said catheter tip,
wherein a distal end of said catheter tip is open, and
wherein a spring constant for the spring-like element is in a range of 0.3 to 25 gF/mm.

16. The catheter of claim 15, wherein said spring-like element is a non-compressible extension spring, and wherein said spring-like element is covered by said longitudinally flexible tube, said longitudinally flexible tube being a flexible polymer material.

17. The catheter of claim 15, wherein said spring-like element is substantially tightly packed.

18. The catheter of claim 15, wherein a distance between said spring-like element of said catheter tip and said distal shoulder of said balloon is selected from 1 mm and 2 mm.

19. The catheter of claim 15, wherein said balloon has a length between said distal and proximal shoulders and a middle point of said length, and said spring-like element of said catheter tip extends proximally with said balloon to a point not exceeding said middle point of said length.

20. The catheter of claim 15, said catheter having a proximal bond between said balloon and an outer tube of said catheter, wherein said spring-like element of said catheter tip extends proximally with said balloon to a point not exceeding said proximal bond.

21. The catheter of claim 15, wherein said spring-like element does not directly abut said distal shoulder of said balloon.

22. A catheter, comprising: a proximal end; a distal end; a balloon having a proximal shoulder and a distal shoulder; and a catheter tip, said catheter tip including a spring-like element having a distal end, a longitudinally flexible tube coupled with said spring-like element, and a radially rigid distal end section located distal of said spring-like element,
wherein said spring-like element provides pushability to said catheter tip and said balloon is mounted on said catheter proximal of said catheter tip, and
wherein a spring constant for the spring-like element is in a range of 0.3 to 25 gF/mm.

23. The catheter of claim 22, wherein said radially rigid distal end section tapers distally along its entire longitudinal length, and wherein said taper is a continuous taper toward the distal end of the catheter.

24. The catheter of claim 22, wherein the longitudinally flexible tube is contiguous with the radially rigid distal end section.

25. The catheter of claim 22, wherein a material of the spring-like element is selected from the group consisting of: stainless steel, cobalt chromium, and nitinol, wherein a material of the longitudinally flexible tube is a flexible polymer material selected from the group consisting of: block co-polymer, polyether block amide (PEBA), and polyurethane, and wherein a material of the radially rigid distal end section is selected from the group consisting of: polyamide, nylon, PEBA, and a co-polymer material.

26. A catheter system, comprising: a catheter having a proximal end and a distal end; a balloon having a proximal shoulder and a distal shoulder; a guide wire; and a catheter tip, said catheter tip comprising:

a longitudinally flexible tube having a luminal side and a vessel wall side; and a spring-like element having a length, wherein the entire length of said spring-like element extends with said longitudinally flexible tube, said spring-like element located at a position selected from the group consisting of: inside said longitudinally flexible tube, and outside said longitudinally flexible tube;

wherein said spring-like element provides pushability to said catheter tip, wherein said spring-like element extends to a distal edge of said catheter tip, wherein the distal edge of the catheter tip does not have less longitudinal flexibility than the guide wire slidably extending therethrough, and wherein a spring constant for the spring-like element is in a range of 0.3 to 25 gF/mm.

27. The catheter system of claim 26, wherein a material of the spring-like element is selected from the group consisting of: stainless steel, cobalt chromium, nitinol, and plastic, and wherein a material of the longitudinally flexible tube is a flexible polymer material selected from the group consisting of: block co-polymer, polyether block amide (PEBA).

28. A catheter system, comprising: a catheter having a proximal end and a distal end; a balloon having a proximal shoulder and a distal shoulder; a guide wire; and a catheter tip, said catheter tip comprising:

a non-compressible spring-like element; and a spacer portion located at a proximal end of said spring-like element;

wherein said spring-like element provides pushability to said catheter tip;

wherein said spring-like element is a wire coil, wherein a distal edge of the catheter tip does not have less longitudinal flexibility than the guide wire slidably extending therethrough, and wherein a spring constant for the spring-like element is in a range of 0.3 to 25 gF/mm.

29. A flexible and pushable catheter tip, comprising:

a longitudinally flexible tube having a luminal side and a vessel wall side; and a spring-like element having a distal end, said spring-like element attached to said flexible tube, said spring-like element located at a position selected from the group consisting of: inside said flexible tube, and outside said flexible tube;

wherein said spring-like element does not extend to a distal edge of said catheter tip, and wherein a spring constant for the spring-like element is in a range of 0.3 to 25 gF/mm.

30. A catheter system, comprising: a catheter having a proximal end and a distal end; a balloon having a proximal shoulder and a distal shoulder; a guide wire; and a catheter tip, said catheter tip comprising:

a longitudinally flexible tube having a luminal side and a vessel wall side; and a spring-like element having a length, wherein the entire length of said spring-like element extends with said longitudinally flexible tube, said spring-like element located at a position selected from the group consisting of: inside said longitudinally flexible tube, and outside said longitudinally flexible tube;

wherein said spring-like element has a distal end and does not extend to a distal edge of said catheter tip, wherein the distal edge of the catheter tip does not have less longitudinal flexibility than the guide wire slidably extending therethrough, and wherein a spring constant for the spring-like element is in a range of 0.3 to 25 gF/mm.

31. The catheter system of claim 30, wherein the longitudinally flexible tube extends beyond the distal end of the spring-like element.

32. The catheter tip of claim 1 or 3, wherein said spring-like element is an extension spring.

33. The catheter tip of claim 1 or 3, wherein said spring-like element further provides radial rigidity to said catheter tip.

34. The catheter tip of claim 1 or 3, wherein said spring-like element tapers distally.

35. The catheter tip of claim 1 or 3, wherein the spring-like element is an accordion tube.

36. The catheter tip of claim 1 or 3, wherein said spring-like element provides simultaneous longitudinal flexibility and pushability to said catheter tip.

37. The catheter tip of claim 1, 3 or 7, wherein said spring-like element is substantially tightly packed and is an extension spring.

38. The catheter tip of, claim 1, 7, 15, 22, 26, 28, 29 or 30, wherein said spring-like element is embedded in a layer of a flexible polymer material.

39. The catheter tip of claim 1, 3, 7 or 29, wherein a material of the spring-like element is selected from the group consisting of: stainless steel, cobalt chromium, and nitinol.

40. The catheter tip of claim 2 or 5, wherein said spacer portion is an extension of said longitudinally flexible tube.

41. The catheter tip of claim 2 or 11, wherein said spring-like element is at least partially inserted into said spacer portion.

42. The catheter tip of claim 3 or 29, wherein the longitudinally flexible tube extends beyond the distal end of the spring-like element.

43. The catheter of claim 15 or 22, wherein said catheter tip includes a spacer portion between a proximal edge of said spring-like element and said distal shoulder of said balloon.

44. The catheter of claim 43, wherein said spacer portion is an extension of said longitudinally flexible tube.

45. The catheter of claim 43, wherein said spring-like element is at least partially inserted into said spacer portion.

46. The catheter of claim 15 or 22, wherein said spring-like element tapers distally.

47. The catheter of claim 15 or 22, wherein the longitudinally flexible tube extends beyond the distal end of the spring-like element.

* * * * *